United States Patent
Fukazu

(10) Patent No.: US 12,193,861 B2
(45) Date of Patent: Jan. 14, 2025

(54) RADIOGRAPHIC IMAGE DISPLAY DEVICE, RADIOGRAPHIC IMAGE DISPLAY METHOD, AND STORAGE MEDIUM

(71) Applicant: KONICA MINOLTA, INC., Tokyo (JP)

(72) Inventor: Kosuke Fukazu, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 274 days.

(21) Appl. No.: 17/691,225

(22) Filed: Mar. 10, 2022

(65) Prior Publication Data
US 2022/0296190 A1    Sep. 22, 2022

(30) Foreign Application Priority Data
Mar. 17, 2021   (JP) ................................. 2021-043012

(51) Int. Cl.
| | | |
|---|---|---|
| A61B 6/46 | (2024.01) | |
| G06F 3/04842 | (2022.01) | |
| G06F 3/0488 | (2022.01) | |
| H04N 23/63 | (2023.01) | |

(52) U.S. Cl.
CPC .............. *A61B 6/465* (2013.01); *A61B 6/469* (2013.01); *G06F 3/04842* (2013.01); *G06F 3/0488* (2013.01); *H04N 23/633* (2023.01)

(58) Field of Classification Search
CPC ..... A61B 6/465; A61B 6/469; G06F 3/04842; G06F 3/0488
See application file for complete search history.

(56) References Cited

U.S. PATENT DOCUMENTS

| | | | | |
|---|---|---|---|---|
| 10,630,879 | B2 * | 4/2020 | Semba | H04N 21/47 |
| 2010/0169833 | A1 | 7/2010 | Arima | |
| 2011/0054295 | A1 * | 3/2011 | Masumoto | A61B 5/4244 600/407 |
| 2013/0329860 | A1 * | 12/2013 | Nonaka | H04L 12/12 378/91 |
| 2016/0041731 | A1 | 2/2016 | Arima | |
| 2017/0163869 | A1 * | 6/2017 | Semba | H04N 21/42204 |
| 2019/0046140 | A1 * | 2/2019 | Hattori | A61B 6/468 |
| 2019/0307327 | A1 * | 10/2019 | Kondo | G16H 30/40 |
| 2021/0174947 | A1 * | 6/2021 | Ohashi | G16H 40/20 |
| 2023/0015883 | A1 * | 1/2023 | Sugiyama | A61B 6/4283 |

FOREIGN PATENT DOCUMENTS

JP      5435937   B2   12/2013

* cited by examiner

*Primary Examiner* — Hugh Maupin
(74) *Attorney, Agent, or Firm* — Holtz, Holtz & Volek PC

(57) ABSTRACT

Provided is a radiographic image display device that includes a display on which a first focus highlight to focus on one imaging condition among multiple imaging conditions and a second focus highlight to focus on a button for displaying a taken image are displayed; and a hardware processor. After completion of an imaging session in the one imaging condition, the hardware processor transitions the first focus highlight to an imaging condition for a next imaging session and transitions the second focus highlight to the button for displaying an image taken in the one imaging condition. The hardware processor controls a transition destination of at least one of the first focus highlight and the second focus highlight according to a type of the next imaging session performed after the imaging session in the one imaging condition.

12 Claims, 9 Drawing Sheets

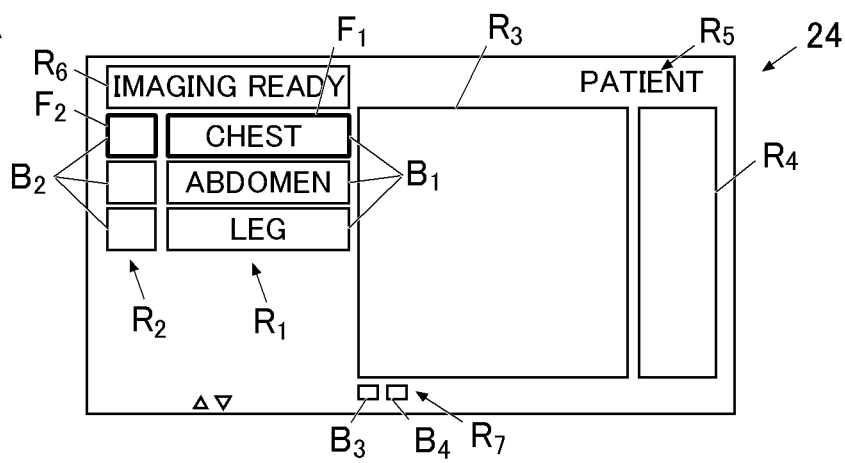
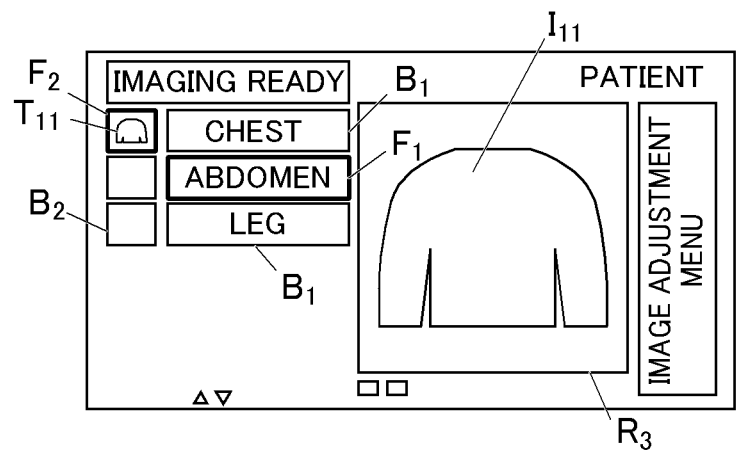
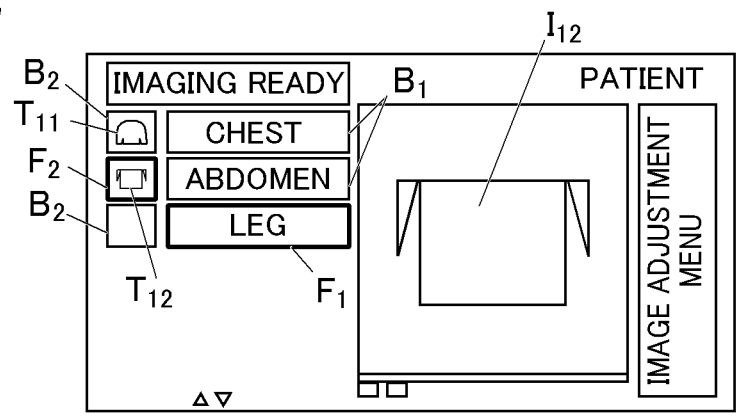

RADIOGRAPHIC IMAGE DISPLAY DEVICE, RADIOGRAPHIC IMAGE DISPLAY METHOD, AND STORAGE MEDIUM

CROSS-REFERENCE TO RELATED APPLICATIONS

The entire disclosure of Japanese Patent Application No. 2021-043012 filed on Mar. 17, 2021 is incorporated herein by reference in its entirety.

BACKGROUND

Technological Field

The present invention relates to a radiographic image display device, a radiographic image display method, and a storage medium.

Description of the Related Art

For a radiographic image display device that displays a list of imaging conditions of multiple radiographic imaging sessions and a list of radiographic images taken in the imaging sessions, there has been a technique of focusing on a specific imaging condition and a specific radiographic image on the lists (differentiating the displaying form or manner from the other imaging conditions and radiographic images), and changing which ones to focus on (stopping focusing on an imaging condition and a radiographic image that have been focused on and newly starting focusing on another imaging condition or radiographic image) when transitioning to the next imaging session (for example, JP5435937B2).

SUMMARY

There are various kinds of radiographic imaging other than regular static imaging, such as long-length imaging (combining radiographic images acquired by imagings of each part) and reimaging after a failure of imaging.

Since imagings in a long-length imaging session are different in the imaging condition such as an imaged region, the radiographic image display device shows each imaging condition separately for the long-length imaging session.

In addition, since reimaging needs to be performed right after failed imaging, the radiographic image display device shows the imaging conditions of the reimaging preceding the imaging condition of the imaging session initially planned.

However, when the next imaging session is not regular static imaging (the imaging condition is shown in a manner different from that for regular static imaging), a conventional radiographic image display device such as the one disclosed in JP5435937B2 has poor usability concerning transition of highlighting (focus) of radiographic images, where a highlight of a radiographic image is transitioned to another one during long-length imaging, for example.

The present invention has been conceived in view of the above-mentioned problem, and has an object of preventing the usability from being reduced when imaging other than static imaging is performed in a radiographic image display device that focuses on imaging conditions and on buttons for displaying radiographic images as well and then changes what to focus on when transitioning to the next imaging.

To achieve at least one of the abovementioned objects, a radiographic image display device reflecting one aspect of the present invention includes:
   a display on which a first focus highlight to focus on one imaging condition among multiple imaging conditions and a second focus highlight to focus on a button for displaying a taken image are displayed; and
   a hardware processor,
   wherein after completion of an imaging session in the one imaging condition, the hardware processor transitions the first focus highlight to an imaging condition for a next imaging session and transitions the second focus highlight to the button for displaying an image taken in the one imaging condition,
   wherein the hardware processor controls a transition destination of at least one of the first focus highlight and the second focus highlight according to a type of the next imaging session performed after the imaging session in the one imaging condition.

To achieve at least one of the abovementioned objects, a radiographic image display method reflecting another aspect of the present invention includes:
   displaying a first focus highlight to focus on one imaging condition among multiple imaging conditions and a second focus highlight to focus on a button for displaying a taken image;
   transitioning, after completion of an imaging session in the one imaging condition, the first focus highlight to an imaging condition for a next imaging session and transitioning the second focus highlight to the button for displaying an image taken in the one imaging condition; and
   controlling a transition destination of at least one of the first focus highlight and the second focus highlight according to a type of the next imaging session performed after the imaging session in the one imaging condition.

To achieve at least one of the abovementioned objects, a storage medium reflecting another aspect of the present invention causes a computer to:
   display a first focus highlight to focus on one imaging condition among multiple imaging conditions and a second focus highlight to focus on a button for displaying a taken image;
   transition, after completion of an imaging session in the one imaging condition, the first focus highlight to an imaging condition for a next imaging session and transition the second focus highlight to the button for displaying an image taken in the one imaging condition;
   control a transition destination of at least one of the first focus highlight and the second focus highlight according to a type of the next imaging session performed after the imaging session in the one imaging condition.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIGS. 4A to 4C show examples of a screen displayed on the console in FIG. 2 (the radiographic image display device in FIG. 3);

DETAILED DESCRIPTION OF THE EMBODIMENTS

Hereinafter, one or more embodiments of the present invention are described with reference to the drawings. However, the technical scope of the present invention is not limited to the following embodiments and illustrated examples.

<1.Overview of Radiographic Imaging System>

First, an overview of a radiographic imaging system (hereinafter referred to as a system 100) in this embodiment is described.

Figure 1:
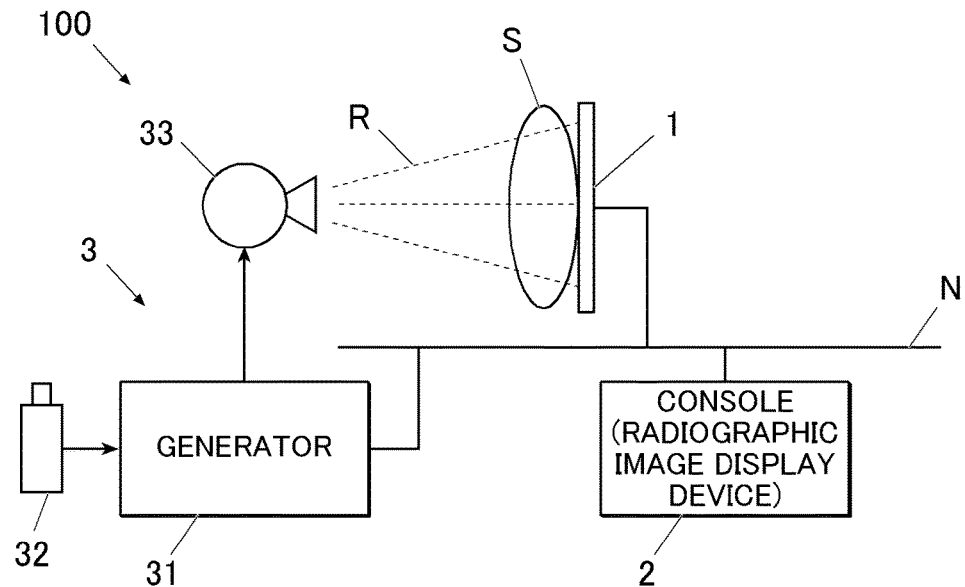
FIG. 1 is a bock diagram showing an example of a radiographic imaging system according to an embodiment of the present invention.

FIG. 1 is a bock diagram showing an example of the system 100.

The system 100 includes, as shown in FIG. 1, a radiation detector (hereinafter referred to as a detector 1), and a console 2.

The system 100 in this embodiment further includes a radiation generating device (hereinafter referred to as a generating device 3).

The components 1 to 3 can communicate with each other via a communication network N (LAN (Local Area Network), WAN (Wide Area Network), the Internet, and the like), for example.

The system 100 may be capable of communicating with a Hospital Information System (HIS), a Radiology Information System (RIS), a Picture Archiving and Communication System (PACS), an analysis device, and the like (not shown).

[1-1. Radiation Generating Device]

The generating device 3 performs radiation emission.

The generating device 3 includes a generator 31, an emission command switch 32, and a radiation source 33.

The emission command switch 32 may include an operation table not shown in the drawings and be connected to the generator 31.

In response to an operation on the emission command switch 32, the generator 31 applies a voltage corresponding to a preset imaging condition(s) (about a subject S (region to be imaged, imaging direction, physique, and the like)) and a condition(s) related to emission of radiation R (tube voltage, tube current, irradiation time, current time product (mAs value), and the like) to the radiation source 33 (tube), and applies an electric current to the radiation source 33 corresponding to the imaging conditions.

When the generator 31 applies a voltage and a current, the radiation source 33 generates a radiation R (X- ray, for example) in an amount according to the applied voltage and current in a mode according to the applied voltage and current.

[1-2. Radiation Detector]

Although not shown in the drawings, the detector 1 includes the followings: a sensor substrate in which pixels having radiation detection elements and switch elements are arranged two-dimensionally (in a matrix shape); a scanning circuit that switches on/off of the respective switch elements; a readout circuit that reads out the amount of charge released from the respective pixels as signal values; a control unit that generates a radiographic image based on the signal values read by the readout circuit; a communication unit that transmits the generated radiographic image data and various signals to the outside and receives various kinds of information and various signals; and the like. In response to receiving radiation, the radiation detection element generates electric charge according to the dose, and the switch elements stores and releases electric charge.

The detector 1 generates a radiographic image depending on the dose of the emitted radiation R by accumulating and releasing electric charges and reading the signal values in synchronization with the timing of the radiation R from the radiation generating device 3.

[1-3. Console]

The console 2 is a radiographic image display apparatus and includes a personal computer and a dedicated device.

The console 2 sets, on at least one of the detector 1 and the generating device 3, the imaging conditions (about the subject S (region to be imaged, imaging direction, physique, and the like)) and the conditions related to emission of radiation R (tube voltage, tube current, irradiation time, current time product (mAs value), and the like).

The console 2 displays the imaging conditions and the radiographic images acquired in imaging.

The console 2 is described later in detail.

[1-4. Overview of Operations of Radiographic Imaging System]

The system 100 configured as described above operates as follows.

First, the console 2 outputs the imaging conditions to at least one of the detector 1 and the generating device 3.

The device to which the imaging conditions are input (at least one of the detector 1 and the generating device 3) sets the input imaging device.

The generating device 3 emits radiation R to the region to be examined of the subject S positioned between the radiation source 33 of the generating device 3 and the detector 1 facing each other with a space in between, and then the detector 1 generates a radiographic image on which the region to be examined is imaged and sends data of the image to the console 2.

Upon receipt of the image data, the console 2 outputs the imaging conditions of the next imaging and displays the acquired radiographic image.

[1-5. Radiographic Imaging System and others]

The system 100 in which the console 2 also functions as the radiographic image display device is described so far, but the radiographic image display device may be provided independently.

Figure 2:
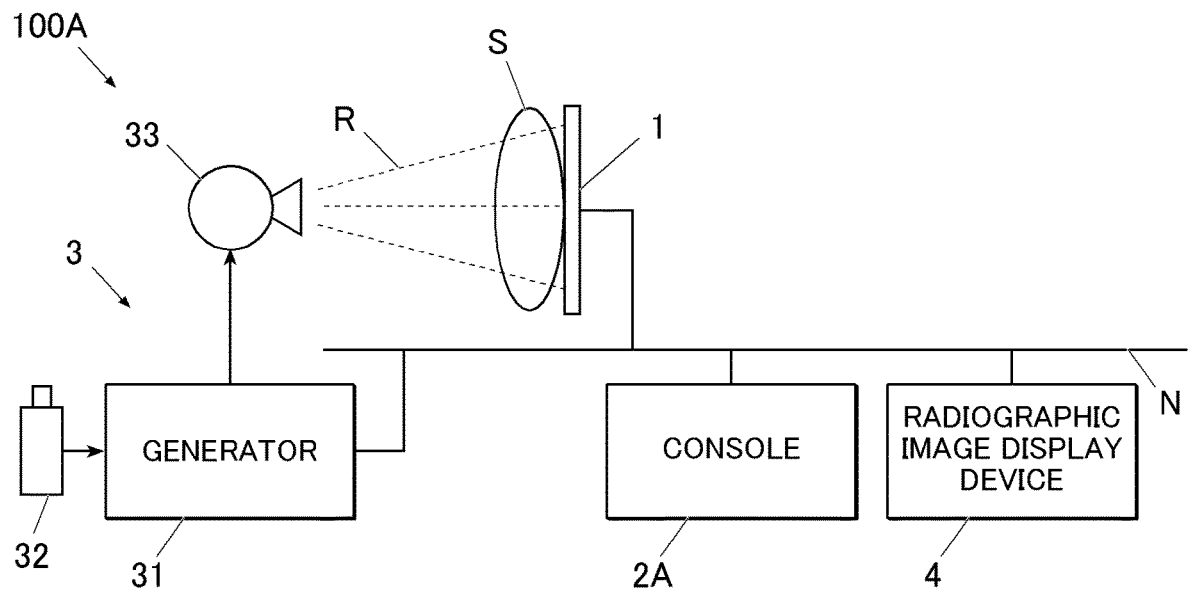
FIG. 2 is a block diagram showing another example of the radiographic imaging system according to the embodiment of the present invention.

Specifically, as shown in FIG. 2, for example, a radiographic imaging system (hereinafter referred to as a system 100A) may otherwise include a console 2A without a function of displaying radiographic images and a radiographic image display device 4 independently provided, in addition to the detector 1 and the generating device 3 described above.

The system 100 may be installed inside an imaging room, or may be movable as a mobile medical vehicle with the generating device 3 and the console 2.

The system 100 or 100A may be an integrated device of the detector 1 and the generating device 3 (for example, a CT (computed tomography) device).

The system 100 may include an imaging table not shown in the drawings (standing position imaging, supine position imaging, long-length imaging) for holding the detector 1.

<2. Details of Console (Radiographic Image Display Device)>

Next, the console 2 in the above-described system 100 (the radiographic image display device 4 in the system 100A) is described in detail.

Figure 3:
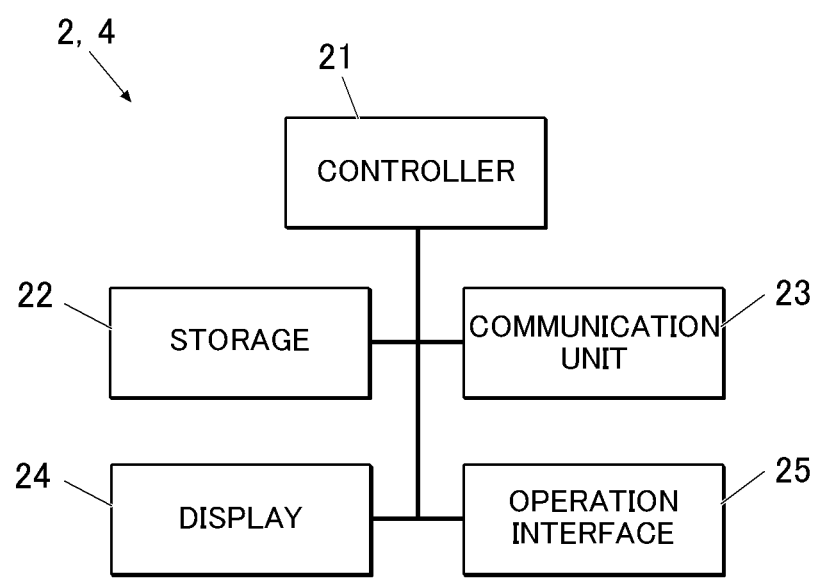
FIG. 3 is a block diagram showing a console in the radiographic imaging system in FIG. 1 (a radiographic image display device in the radiographic imaging system in FIG. 2)

FIG. 3 is a block diagram showing the console 2 (the radiographic image display device 4), and FIGS. 4 to 10 show examples of the screens displayed on the console 2 (the radiographic image display device 4).

[2-1. Detailed Configuration of Console]

The console 2 (the radiographic image display device 4) includes, as shown in FIG. 3, a controller 21, a storage 22, a communication unit 23, a display 24, and an operation interface 25. The components 21 to 25 are electrically connected to each other by a bus or the like.

The controller 21 includes a CPU (central processing unit) and a RAM (random access memory).

The CPU of the controller 21 reads various programs stored in the storage 22, loads them in the RAM, executes various kinds of processing according to the loaded programs, and centrally controls the operations of the components of the console 2 (the radiographic image display device 4).

The storage 22 includes a non-volatile memory and a hard disk.

The storage 22 stores various programs executed by the controller 21 (including the radiographic image display program), parameters necessary for executing the programs, and the like.

The storage 22 may be capable of storing image data of radiographic images acquired from other devices (for example, the detector 1).

The communication unit 23 may include a communication module.

The communication unit 23 sends and receives various signals and data to and from other devices (the detector 1, the generating device 3, and the like) connected via a communication network N (LAN (local area network), WAN (wide area network), the Internet, or the like) by wire or wirelessly.

The display 24 displays various screens used for diagnoses by the user.

The display 24 is a liquid crystal display (LCD), a cathode ray tube (CRT), or the like, for example.

The display 24 displays radiographic images according to the image signals received from the controller 21.

The operation interface 25 includes, for example, a keyboard (cursor keys, numeric input keys, function keys, and the like), a pointing device (a mouse and the like), a touch panel overlaid on the surface of the display 24.

The operation interface 25 outputs control signals corresponding to input operations by the user to the controller 21.

The console 2 may not include the display 24 and the operation interface 25, but may receive control signals from an input device provided separately from the console 2 via the communication unit 23 or output image signals to a display (monitor) provided separately from the console 2, for example.

In the case where some other device (for example, the analysis device) includes a display and an operation interface, the console 2 may receive control signals from the operation interface of that device and output image signals to that device (the display and the operation interface may be shared with the other device).

[2-2. Operations of Console]

The console 2 (the radiographic image display device 4) configured as described above operates as follows.

(Display Processing)

The controller 21 executes display processing according to the radiographic image display program, triggered by satisfaction of a predetermined condition(s).

The predetermined conditions include, for example, power-on of the console 2 (the radiographic image display device 4), reception of an imaging order from the other device, acquisition of image data from the other device, reception of a predetermined control signal from the other device, and reception of an input operation to the operation interface 25.

The controller 21 displays an imaging screen as shown in FIG. 4A, for example, on the display 24 in this display processing.

The imaging screen includes a first buttons display area $R_1$, a second buttons display area $R_2$, and an image display area $R_3$.

The imaging screen in this embodiment further includes an image adjustment menu display area $R_4$, a subject information display area $R_5$, a ready state display area $R_6$, and an operation buttons display area $R_7$.

The first buttons display area $R_1$ is an area for displaying the first buttons $B_1$.

The controller 21 displays the first buttons $B_1$ according to the imaging order acquired from the other device in the first buttons display area $R_1$.

The first buttons $B_1$ in this embodiment are vertically arranged.

The controller 21 shows the imaging conditions respectively on the first buttons $B_1$.

The imaging conditions shown on the first buttons $B_1$ in FIG. 4 and the like are the regions to be imaged, but the controller 21 may show other imaging conditions on the first buttons $B_1$.

The first buttons display area $R_1$ shows a first focus highlight $F_1$.

The first focus highlight $F_1$ shows one of the imaging conditions in a focused state.

The first focus highlight $F_1$ in this embodiment shows the imaging condition of the current or next imaging session in a focused state.

As described above, the imaging conditions are respectively shown on the first buttons $B_1$, and therefore the first focus highlight $F_1$ shows the first button $B_1$ in a focused state.

The first focus highlight $F_1$ in this embodiment is changing the color of the button edge or superimposing a frame in a different color but in the same shape as the button edge.

The focus may also be widening the button edge or changing the overall color of the button.

The second buttons display area $R_2$ is an area for the second buttons $B_2$.

The controller 21 shows the second buttons $B_2$ of the same number as the first buttons $B_1$ in the second buttons display area $R_2$.

The second buttons $B_2$ in this embodiment are respectively arranged next to the first buttons $B_1$.

The controller 21 shows taken radiographic images respectively on the second buttons $B_2$.

The radiographic images are shown as thumbnails on the second buttons $B_2$ in this embodiment.

A second focus highlight $F_2$ is shown in the second buttons display area $R_2$.

The second focus highlight $F_2$ shows the second button $B_2$ showing the radiographic image taken in the imaging condition on the first button $B_1$ next to the said second button $B_2$ in a focused state.

The second focus highlight $F_2$ in this embodiment is changing the color of the button edge or superimposing a frame in a different color but in the same shape as the button edge, similarly to the first focus highlight $F_1$.

The form of the second focus highlight $F_2$ may be different from that of the first focus highlight $F_1$.

The image display area $R_3$ is an area for displaying a radiographic image.

The controller 21 shows the radiographic image corresponding to the thumbnail on the second button $B_2$ shown with the second focus highlight $F_2$ in the image display area $R_3$.

The image adjustment display area $R_4$ is an area for displaying the operation buttons for performing adjustment of the radiographic image shown in the image display area $R_3$.

The subject information display area $R_5$ is an area for displaying information on the subject (for example, subject name).

The ready state display area $R_6$ is an area for displaying the ready state of the next radiographic imaging session.

In the detector 1 and the generating device 3, when an imaging session in the imaging condition on the first button $B_1$ shown with the first focus highlight $F_1$, an indication that imaging is possible is displayed (for example, message "imaging ready").

The operation buttons display area $R_7$ is an area for displaying buttons for performing various operations on the imaging screen.

The buttons for various operations include an imaging error button $B_3$ and a transition limit button $B_4$.

The controller 21 specifies a radiographic image as an error image (judging the imaging of the radiographic image as a failure) if the error button $B_3$ is operated while the radiographic image is displayed in the image display area $R_3$.

The controller 21 and the display 24 function as a display means by performing the operations described above.

The controller 21 performing the above-described display processing corresponds to displaying in the radiographic image display method.

(Display Control Processing)

The controller 21 performs display control processing along with proceeding of the imaging session.

Specifically, before the first imaging session is started, the controller 21 displays the imaging condition of the imaging session to be performed on a first buttons $B_1$ in the first buttons display area $R_1$, as shown in FIG. 4A.

Here, the controller 21 shows the first focus highlight $F_1$ on the first button $B_1$ (at the top in this example) indicating the imaging condition of the first imaging session.

The controller 21 is then set to the state in which the controller 21 can output the imaging condition corresponding to the first button $B_1$ shown with the first focus highlight $F_1$ to at least one of the detector 1 and the generating device 3 via the communication unit 23.

The controller 21 shows the second focus highlight $F_2$ on the second button $B_2$ next to the first button $B_1$ indicating the imaging condition of the first imaging session.

At this stage, since a radiographic image is not yet acquired, thumbnails are not shown on any of the second buttons $B_2$ including the second button $B_2$ next to the first button $B_1$ indicating the imaging condition of the first imaging session.

When the imaging session in the first imaging condition (regular static imaging: chest) is done, the controller 21 shows a thumbnail $T_{11}$ of the radiographic image taken in the first imaging condition on the second button $B_2$ next to the first button $B_1$ indicating the imaging condition of the first imaging session, as shown in FIG. 4B.

Here, the controller 21 continues to show the concerning second button $B_2$ with the second focus highlight $F_2$.

Here, the controller 21 transitions the first focus highlight $F_1$ to the first button $B_1$ (the second one from the top in this example) indicating the imaging condition of the second imaging session (regular static imaging: abdomen).

The controller 21 displays a radiographic image I, corresponding to the thumbnail $T_{11}$ on the second button $B_2$ with the second focus highlight $F_2$ in the image display area $R_3$.

As a result, the user can adjust a radiographic image and judge an imaging error right after imaging. The user can also adjust a radiographic image and perform the next imaging session in parallel.

The operations for performing regular static imaging without problems are described so far, but the imaging using the system 100 may be or may not be regular static imaging.

Thus, the controller 21 further performs processing for controlling a transition destination of at least one of the first focus highlight $F_1$ and the second focus highlight $F_2$ according to the type of the next imaging session performed after one imaging session in a certain imaging condition.

Specifically, in the case where the type of the next imaging session performed after one imaging session in a certain imaging condition is static imaging (a first imaging type), when the imaging session in the certain imaging condition is done, the controller 21 transitions the first focus highlight $F_1$ to the first button $B_1$ (the third one from the top in this example) indicating the imaging condition of the next imaging session, and transitions the second focus highlight $F_2$ to the second button $B_2$ (the second one from the top in this example) showing the thumbnail $T_{12}$ of the radiographic image taken in the certain imaging condition as shown in FIG. 4C.

The controller 21 displays a radiographic image $I_{12}$ corresponding to the thumbnail on the second button $B_2$ with the second focus highlight $F_2$ in the image display area $R_3$.

On the other hand, in the case where the type of the next imaging session performed after one imaging session in a certain condition is a second type of imaging, the controller 21 transitions the first focus highlight $F_1$ to one of the first buttons $B_1$ indicating an imaging condition other than the imaging condition of the next imaging session, or transitions the second focus highlight $F_2$ to one of the second buttons $B_2$ other than the second button $B_2$ with the radiographic image taken in the certain imaging condition.

The second type of imaging may be long-length imaging, reimaging, or the like.

Long-length imaging is to generate a combined image by taking multiple radiographic images and combining the multiple taken radiographic images.

Reimaging is to take an image over again after imaging in a certain condition has failed (resulted in an error).

Figure 5A:
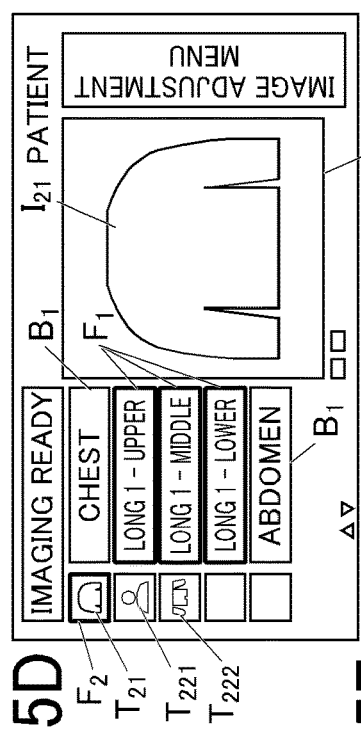
FIGS. 5A to 5F show examples of a screen displayed on the console in FIG. 2 (the radiographic image display device in FIG. 3)
Figure 5B:
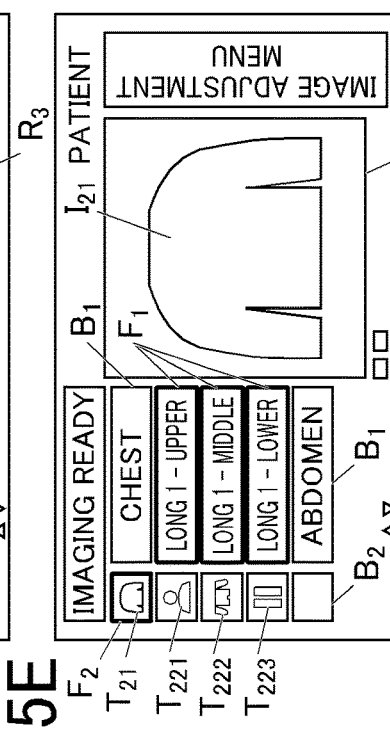
Figure 5C:
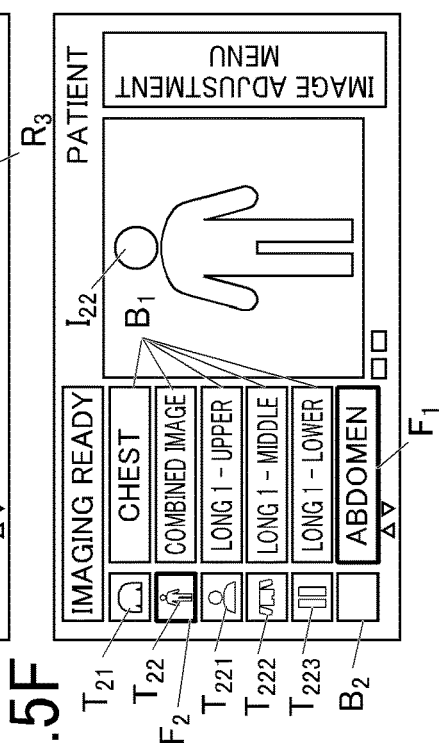
Figure 5D:
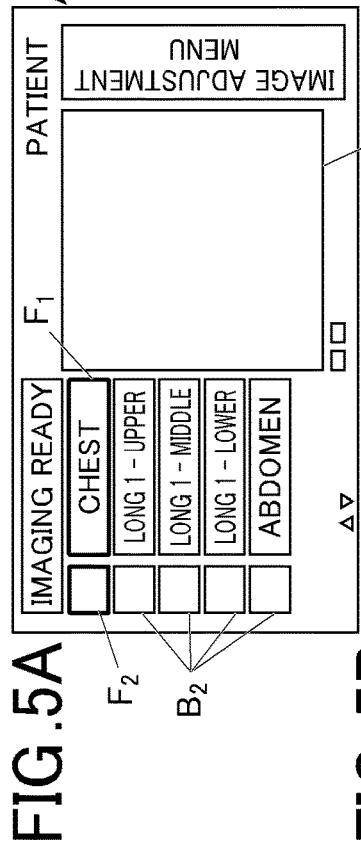
Figure 5E:
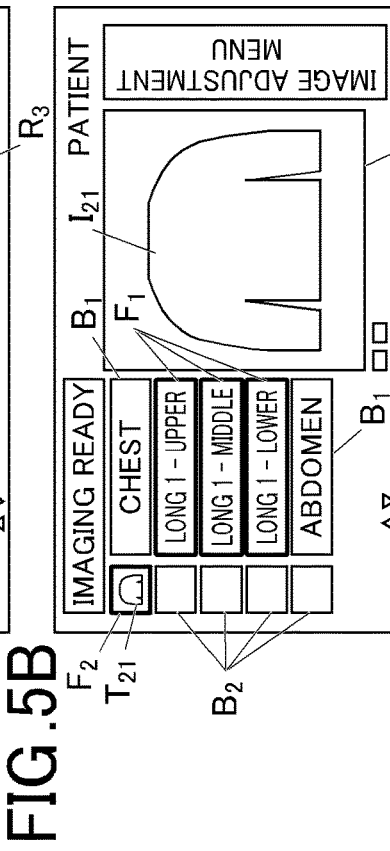

Specifically, in the case where the next imaging session after one imaging session in a certain imaging condition (static imaging of the chest as shown in FIG. 5A in this example) is long-length imaging, the controller 21 shows the first focus highlight $F_1$ on the multiple (three) first buttons $B_1$ indicating the imaging conditions of imagings included in the long-length imaging session as shown in FIGS. 5B to 5E.

The controller 21 successively displays thumbnails $T_{221}$ to $T_{223}$ of the radiographic images before combining on the second buttons $B_2$ along with proceeding of the long-length imaging session.

On the other hand, the controller 21 prohibits transition of the second focus highlight $F_2$ until the long-length imaging session is done (not transitioning the focus highlight $F_2$ to the second buttons $B_2$ with the thumbnails $T_{221}$ to $T_{223}$ of the radiographic images before combining).

Meanwhile, the controller 21 displays the radiographic image $I_{21}$ (taken in the imaging session in the certain imaging condition) corresponding to the thumbnail on the second button $B_2$ shown with the second focus highlight $F_2$ in the image display area $R_3$.

Figure 5F:
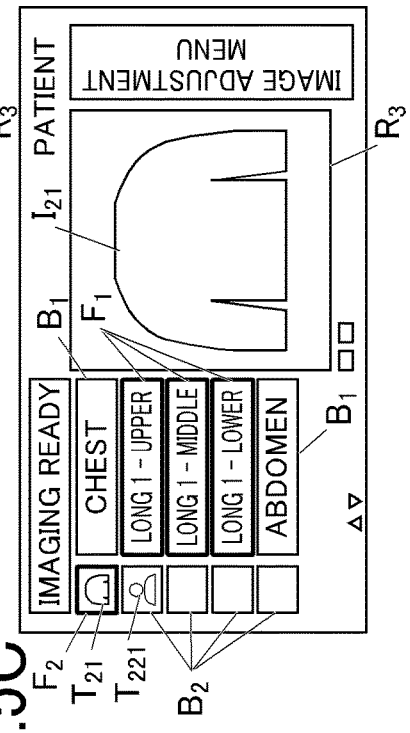

After the long-length imaging session is done, the controller 21 shows the first button $B_1$ (the second one from the top in this example) indicating that the image is a combined image between the first button $B_1$ indicating the certain imaging condition (the first one from the top in this example) and the first button $B_1$ indicating the imaging condition of the next long-length imaging session, and shows the second button $B_2$ with a thumbnail $T_{22}$ of the combined image next to the concerning (newly shown) first button $B_1$, as shown in FIG. 5F.

The controller 21 transitions the second focus highlight $F_2$ to the second button $B_2$ with the thumbnail $T_{22}$ of the combined image.

The controller 21 displays the radiographic image (combined image $I_{22}$) corresponding to the thumbnail of the button $B_2$ shown with the second focus highlight $F_2$ in the image display area $R_3$.

In FIG. 5, the long-length imaging session is performed after the static imaging session is done, but in the case where another long-length imaging session is performed after a long-length imaging session, the controller 21 also performs the display control in almost the same way as the long-length imaging session after the static imaging session, as shown in FIG. 6, for example.

Figure 6A:
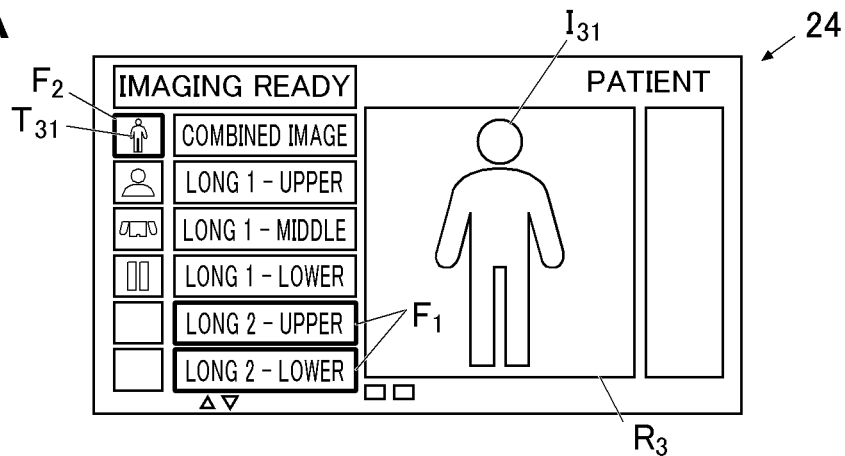
FIGS. 6A to 6C show examples of a screen displayed on the console in FIG. 2 (the radiographic image display device in FIG. 3)

That is, when one long-length imaging session is done, a first button $B_1$ indicating that the image is a combined image acquired in the one long-length imaging session and a second button $B_2$ with a thumbnail $T_{31}$ of the combined image are shown, the controller 21 transitions the second focus highlight $F_2$ to the second button $B_2$ with the combined image, as shown in FIG. 6A.

Figure 6B:
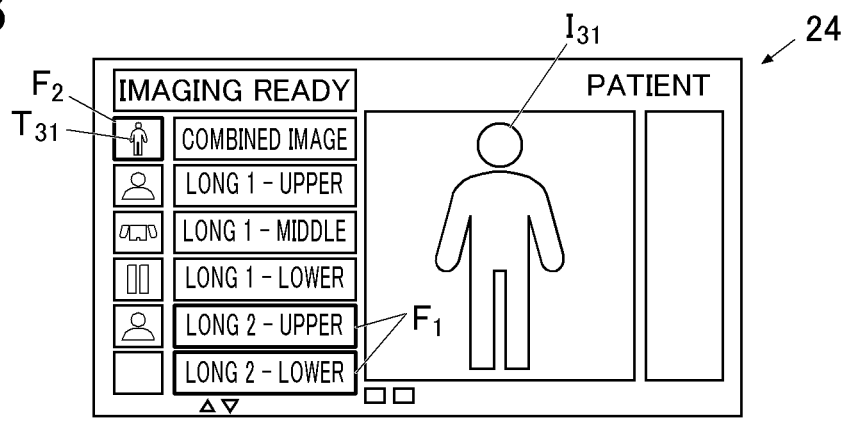
Figure 6C:
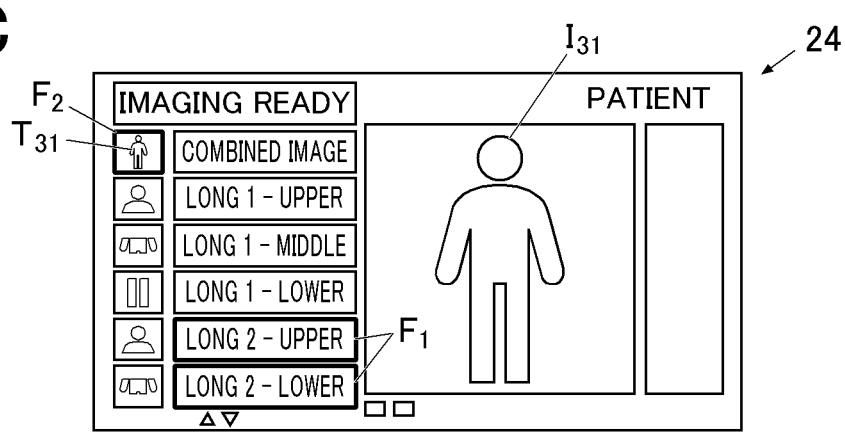
Figure 7A:
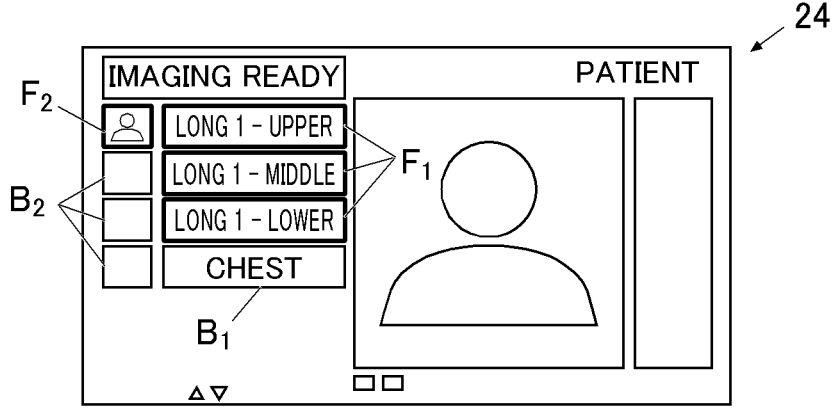
FIGS. 7A to 7D show examples of a screen displayed on the console in FIG. 2 (the radiographic image display device in FIG. 3)
Figure 7B:
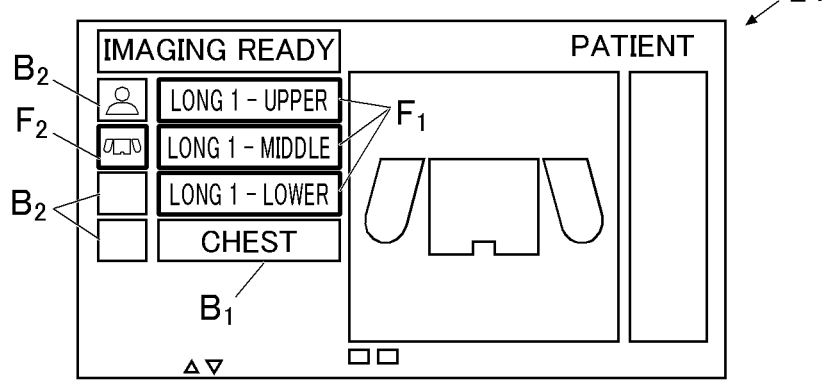
Figure 7C:
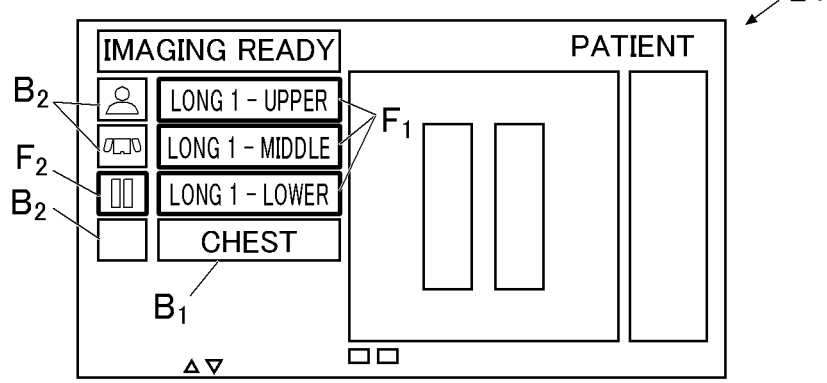
Figure 7D:
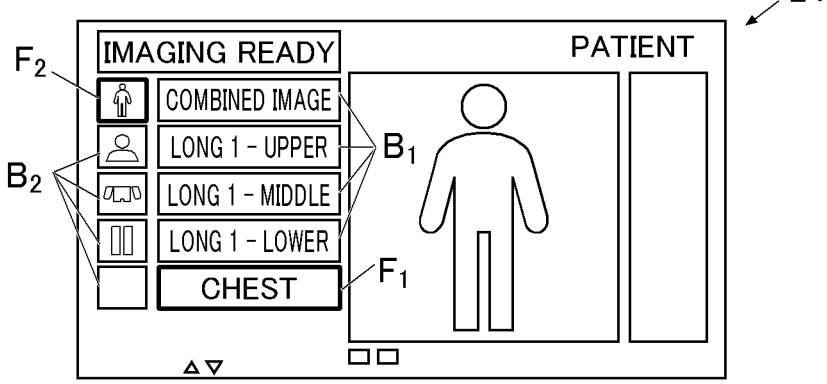

While each imaging in the next long-length imaging session is being performed (until a long-length imaging session is done and a combined image acquired in the next long-length imaging is displayed), the controller 21 continues to show the second focus highlight $F_2$ on the second button $B_2$ with the thumbnail $T_{31}$ of the combined image, as shown in FIGS. 6B and 6C.

Meanwhile, the controller 21 displays the radiographic image (the combined image $I_{31}$ taken in one long-length imaging session) corresponding to the thumbnail $T_{31}$ on the second button $B_2$ shown with the second focus highlight $F_2$ in the image display area $R_3$.

In FIGS. 5 and 6, the transition of the second focus highlight $F_2$ is prohibited until the long-length imaging session is done, but the controller 21 may transition the second focus highlight $F_2$ along with proceeding of the imagings included in the long-length imaging session according to a predetermined operation for cancelling the transition prohibition as shown in FIG. 7, for example.

Figure 8A:
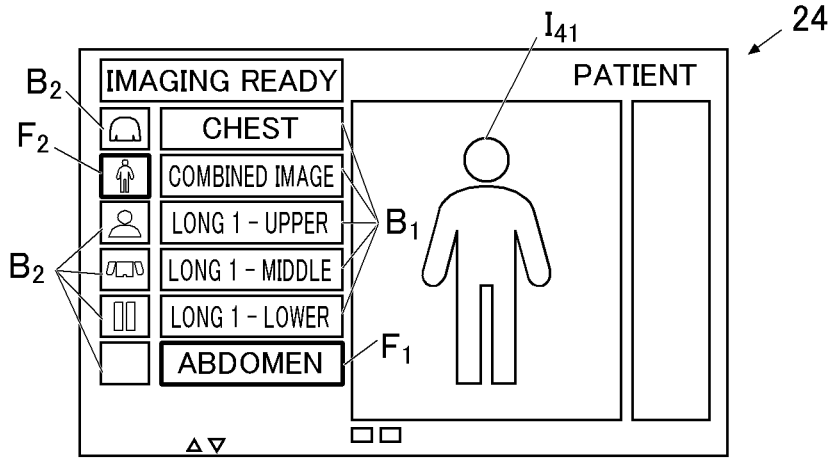
FIGS. 8A to 8C show examples of a screen displayed on the console in FIG. 2 (the radiographic image display device in FIG. 3)
Figure 8B:
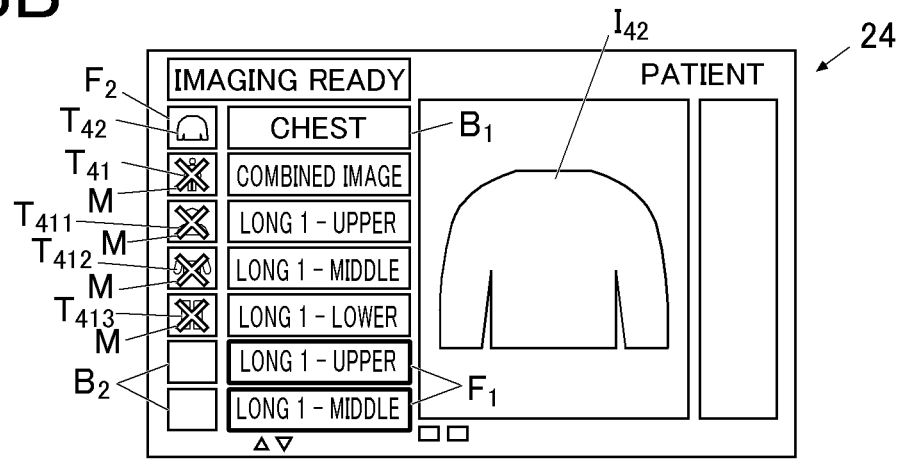

On the other hand, when the type of the next imaging session after the imaging session in the certain imaging condition (for example, the long-length imaging session corresponding to the second to fifth first buttons $B_1$ in FIG. 8A) is reimaging (when the user judges that the combined image $I_{41}$ in FIG. 8A as an error and operates the error button $B_3$ (until that user operation, the first focus highlight $F_1$ is shown on the first button $B_1$ indicating the imaging condition of the imaging session after the next one (static imaging of the abdomen in this example)), the controller 21 shows a mark M (for example, "X") indicating that the corresponding image is an error image on the second buttons $B_2$ with the thumbnails $T_{41}$ and $T_{411}$ to $T_{413}$ of the radiographic images taken in the imaging session in the certain imaging condition as shown in FIG. 8B.

The controller 21 newly shows a first button $B_1$ indicating the imaging condition of the reimaging session under the first button $B_1$ indicating the imaging condition of the next imaging session (after the failed imaging), and shows a second button $B_2$ without a thumbnail next to the concerning (newly shown) first button $B_1$.

Here, the first button for the imaging session initially planned after the next imaging session (the imaging condition of the static imaging of the abdomen in FIG. 8A) is not shown because it is framed out of the imaging screen.

The controller 21 transitions the first focus highlight $F_1$ to the first button $B_1$.

The controller 21 transitions the second focus highlight $F_2$ to the second button $B_2$ with the thumbnail $T_{42}$ of the radiographic image taken before the imaging session in the certain condition (the chest image corresponding to the first button $B_1$ at the top in this example).

The controller 21 displays the radiographic image $I_{42}$ of the chest corresponding to the thumbnail $T_{42}$ on the second button $B_2$ with the second focus highlight $F_2$ in the image display area $R_3$.

Figure 8C:
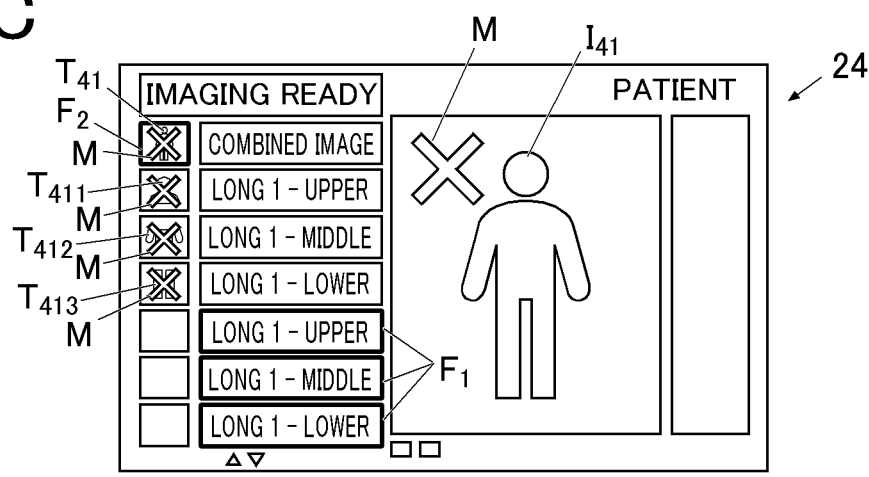

In the case where no imaging was performed before the failed imaging session in the certain condition, the controller 21 continues to show the second focus highlight $F_2$ on the second button $B_2$ with the thumbnail $T_{41}$ of the radiographic image judged as an error (the combined image in this example), as shown in FIG. 8C, for example.

The controller 21 shows the radiographic image (the combined image $I_{41}$) corresponding to the thumbnail on the second button $B_2$ with the second focus highlight $F_2$ in the image display area $R_3$.

The controller 21 shows a mark M (for example, "X") indicating that the corresponding image is an error on the radiographic image $I_{41}$ acquired in the imaging session in the certain imaging condition (the imaging judged as an error) and the corresponding second buttons $B_2$ with the thumbnails $T_{41}$ and T411 to T413.

Figure 9A:
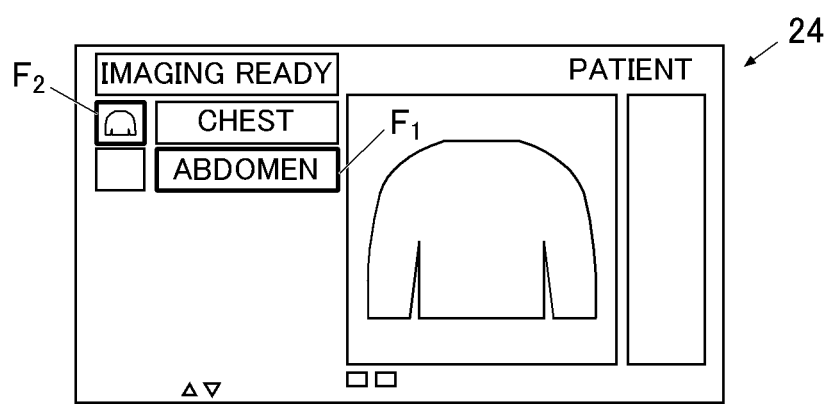
FIGS. 9A to 9B show examples of a screen displayed on the console in FIG. 2 (the radiographic image display device in FIG. 3)
Figure 9B:
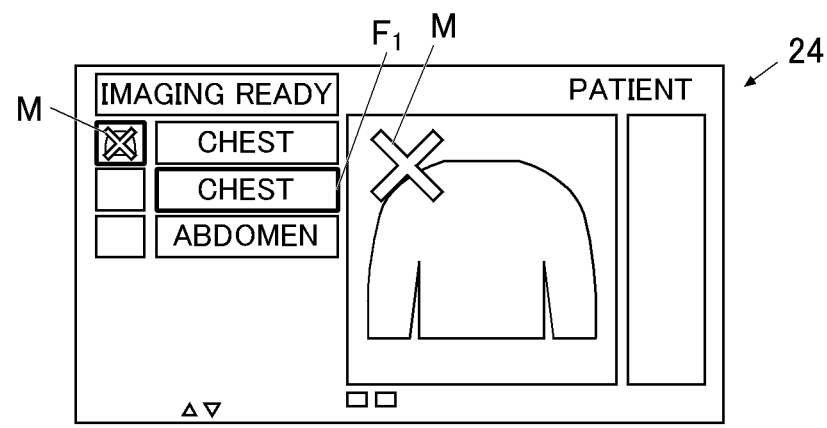

Reimagings are required for a long-length imaging session in the example of FIGS. 8, but when reimaging is required for a static imaging session, the controller 21 performs display control similarly to the long-length imaging session, as shown in FIG. 9, for example.

In response to a user operation on the transition limit button $B_4$, the controller 21 prohibits transition of the second focus highlight $F_2$ even when the next imaging session is complete and the thumbnail of the radiographic image acquired in the next imaging session is shown on the second button $B_2$.

For example, in the case where the transition limit button $B_4$ is operated to prohibit the transition before the next imaging session (for example, static imaging of the abdomen shown in FIG. 10A) is started, the controller 21 does not transition the second focus highlight $F_2$ (continues to show the second focus highlight $F_2$ on the second button $B_2$ with the thumbnail $T_{43}$ of the static image of the chest obtained by static imaging of the chest) when the next imaging sessions (static imaging of the abdomen and part of long-length imaging) are complete and the thumbnails $T_{41}$ and $T_{42}$ are shown on the corresponding second buttons $B_2$.

As a result, the user who finds it difficult to adjust a radiographic image along with proceeding of imaging can perform adjustment at her/his own speed.

Figure 10A:
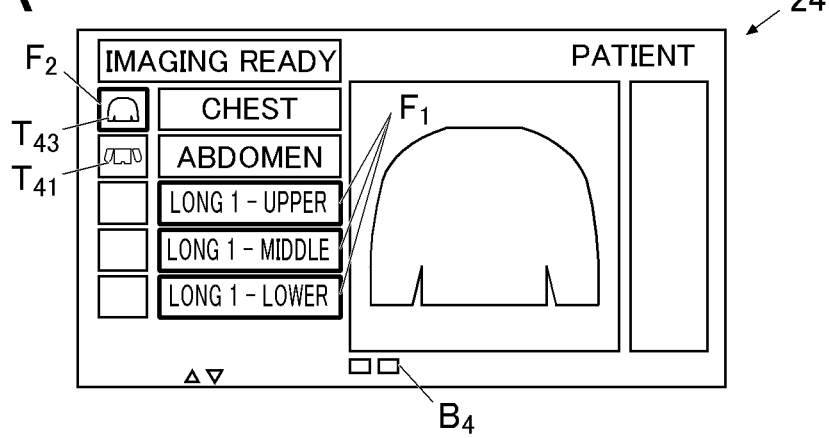
FIGS. 10A to 10C show examples of a screen displayed on the console in FIG. 2 (the radiographic image display device in FIG. 3).
Figure 10B:
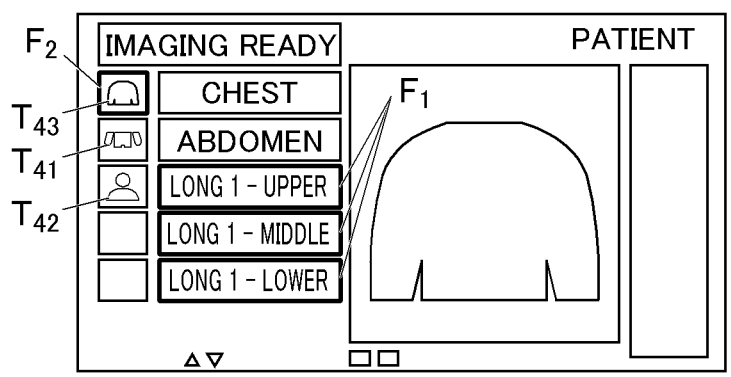
Figure 10C:
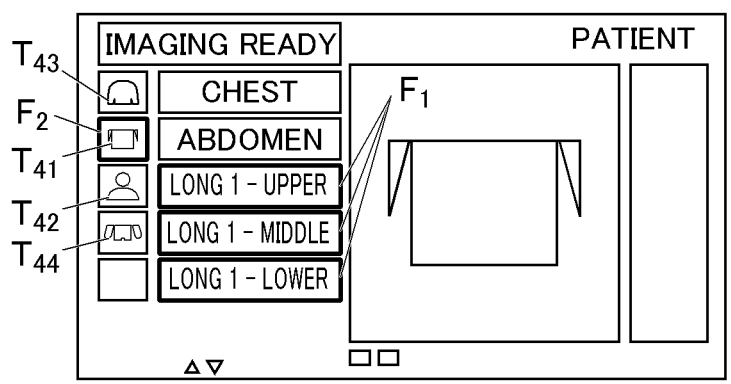

However, even in the case where the transition of the second focus highlight $F_2$ is prohibited, the controller 21 transitions the second focus highlight $F_2$ to the operated second button $B_2$ as shown in FIG. 10C when the second button $B_2$ shown without the second focus highlight $F_2$ is operated.

Though not shown in the drawings, the controller 21 also transitions the second focus display $F_2$ to the operated second button $B_2$ when the second buttons $B_2$ with the thumbnails $T_{42}$ and $T_{44}$ of the radiographic images acquired in the long-length imaging session are operated.

The controller 21 and the display 24 function as display control means by performing the operations described above.

The controller 21 performing the above-described display control processing corresponds to display control in the radiographic image display method.

<3. Advantageous Effects>

As described hereinbefore, the console 2 (the radiographic image display device 4) includes the display 24 on which the first focus highlight $F_1$ and the second focus highlight $F_2$ are displayed and the controller 21 (the hardware processor). After completion of an imaging session in a certain imaging condition, the controller 21 transitions the first focus highlight $F_1$ to an imaging condition for the next imaging session (the first button $B_1$) and transitions the second focus highlight $F_2$ to a button for displaying an image taken in the certain imaging condition (the second button $B_2$). The controller 21 controls a transition destination of at least one of the first focus highlight F, and the second focus highlight $F_2$ according to the type of the next imaging session performed after the imaging session in the certain imaging condition.

Therefore, the console 2 (the radiographic image display device 4) makes it possible to maintain the usability in imaging different from regular static imaging.

<4. Misc.>

Needless to say, the present invention is not limited to the above embodiment and can be appropriately modified without departing from the scope of the present invention.

For example, the system 100 may support one-shot long-length imaging in which multiple radiographic images are generated by single emission of radiation R to be combined by using multiple detectors 1 simultaneously.

In that case, the operations of the console 2 (the radiographic image display device 4) in the one-shot imaging may be the same as those in the regular static imaging.

The system 100 may support movie recording for generating multiple frames.

In that case, as in the one-shot imaging, the operations of the console 2 (the radiographic image display device 4) in the movie recording may be the same as those in the regular static imaging.

The above description discloses an example of using a hard disk, a semiconductor nonvolatile memory and the like as the computer readable medium of the program for radiographic image display according to the present invention. However the present invention is not limited to the example. A portable recording medium such as a CD-ROM can be applied as other computer readable mediums. A carrier wave is also applied as a medium providing the data of the program for radiographic image display according to the present invention via a communication line.

What is claimed is:

1. A radiographic image display device comprising:
   a display; and
   a hardware processor that is configured to:
   control the display to display a plurality of first buttons and a plurality of second buttons, wherein the plurality of first buttons are respectively associated with the plurality of second buttons, wherein a plurality of imaging conditions are respectively displayed on the plurality of first buttons, and wherein the plurality of second buttons are for displaying an image taken in the imaging condition displayed on the associated first button, and
   control display of a first focus highlight for highlighting a first button from among the plurality of first buttons on which the plurality of imaging conditions are respectively displayed, and control display of a second focus highlight for highlighting a second button among the plurality of second buttons, wherein the hardware processor performs display control such that the first button highlighted by the first focus highlight is displayed in a display mode different from a display mode of other first buttons which are not highlighted from among the plurality of first buttons, and such that the second button highlighted by the second focus highlight is displayed in a display mode different from a display mode of other second buttons which are not highlighted from among the plurality of second buttons,
   wherein the hardware processor controls display so that the first focus highlight highlights a first button among the plurality of first buttons on which a first imaging condition for a first imaging session from among the plurality of imaging conditions is displayed,
   wherein after completion of the first imaging session in the first imaging condition, the hardware processor displays an image taken in the first imaging condition on the associated second button, controls display of the second focus highlight to highlight the second button on which the image taken in the first imaging condition is displayed, and transitions the first focus highlight to highlight another first button among the plurality of first buttons on which a second imaging condition for a next imaging session is displayed, such that after completion of the first imaging session and before completion of the next imaging session, the first focus highlight highlights said another first button on which the second imaging condition is displayed and the second focus highlight concurrently highlights the second button on which the image taken in the first imaging condition of the completed first imaging session is displayed, wherein the hardware processor controls a transition destination of at least one of the first focus highlight and the second focus highlight according to a type of the next imaging session performed after the first imaging session in the first imaging condition.

2. The radiographic image display device according to claim 1, wherein, when the type of the next imaging session performed after the first imaging session in the first imaging condition is a first imaging type, the hardware processor, in response to completion of the first imaging session in the first imaging condition, transitions the first focus highlight to highlight another first button among the plurality of first buttons on which an imaging condition for the next imaging session is displayed and transitions the second focus highlight to highlight the second button for displaying the image taken in the first imaging session in the first imaging condition, and wherein when the type of the next imaging session performed after the first imaging session in the one first imaging condition is a second imaging type, the hardware processor transitions the first focus highlight to highlight another first button among the plurality of first buttons on which an imaging condition other than the imaging condition for the next imaging session is displayed or transitions the second focus highlight to highlight a second button other than the second button for displaying the image taken in the first imaging session in the one first imaging condition.

3. The radiographic image display device according to claim 1, wherein when the type of the next imaging session performed after the first imaging session in the first imaging condition is reimaging, the hardware processor transitions the second focus highlight to a second button among the plurality of second buttons for displaying an image taken before the first imaging session in the first imaging condition.

4. The radiographic image display device according to claim 1, wherein the type of the next imaging session performed after the first imaging session in the first imaging condition is long-length imaging in which multiple images are taken to generate a combined image of the taken multiple images.

5. The radiographic image display device according to claim 4, wherein the hardware processor prohibits transition of the second focus highlight until completion of the long-length imaging and transitions the second focus highlight to highlight a second button among the plurality of second buttons for displaying the combined image after the completion of the long-length imaging.

6. The radiographic image display device according to claim 3, wherein when the type of the next imaging session performed after the first imaging session in the first imaging condition is reimaging, the hardware processor transitions the first focus highlight to highlight another first button among the plurality of first buttons on which an imaging condition for the reimaging is displayed.

7. The radiographic image display device according to claim 1, wherein when the second button for displaying the taken image is operated, the hardware processor transitions the second focus highlight to the operated second button.

8. The radiographic image display device according to claim 1, wherein a thumbnail of the taken image is shown on the second button for displaying the taken image.

9. The radiographic image display device according to claim 1, a button for prohibiting transition of the second focus highlight is displayed.

10. The radiographic image display device according to claim 1, a button for making an imaging condition ready for output is focused on by the first focus highlight.

11. A radiographic image display method executed by a hardware processor, the method comprising:

controlling a display to display a plurality of first buttons and a plurality of second buttons, wherein the plurality of first buttons are respectively associated with the plurality of second buttons, wherein a plurality of imaging conditions are respectively displayed on the plurality of first buttons, and wherein the plurality of second buttons are for displaying an image taken in the imaging condition displayed on the associated first button;

controlling display of a first focus highlight for highlighting a first button from among the plurality of first buttons on which the plurality of imaging conditions are respectively displayed, and controlling display of a second focus highlight for highlighting a second button among the plurality of second buttons, wherein the display control is performed such that the first button highlighted by the first focus highlight is displayed in a display mode different from a display mode of other first buttons which are not highlighted from among the plurality of first buttons, and such that the second button highlighted by the second focus highlight is displayed in a display mode different from a display mode of other second buttons which are not highlighted from among the plurality of second buttons;

controlling display so that the first focus highlight highlights a first button among the plurality of first buttons on which a first imaging condition for a first imaging session from among the plurality of imaging conditions is displayed;

after completion of the first imaging session in the one first imaging condition, displaying an image taken in the first imaging condition on the associated second button, controlling display of the second focus highlight to highlight the second button on which the image taken in the first imaging condition is displayed, and transitioning the first focus highlight to highlight another first button among the plurality of first buttons on which a second imaging condition for a next imaging session is displayed, such that after completion of the first imaging session and before completion of the next imaging session, the first focus highlight highlights said another first button on which the second imaging condition is displayed and the second focus highlight concurrently highlights the second button on which the image taken in the first imaging condition of the completed first imaging session is displayed; and controlling a transition destination of at least one of the first focus highlight and the second focus highlight according to a type of the next imaging session performed after the first imaging session in the first imaging condition.

12. A non-transitory storage medium storing a computer-readable program that causes a computer to:

control a display to display a plurality of first buttons and a plurality of second buttons, wherein the plurality of first buttons are respectively associated with the plurality of second buttons, wherein a plurality of imaging conditions are respectively displayed on the plurality of first buttons, and wherein the plurality of second buttons are for displaying an image taken in the imaging condition displayed on the associated first button, control display of a first focus highlight for highlighting a first button from among the plurality of first buttons on which the plurality of imaging conditions are respectively displayed, and control display of a second focus highlight for highlighting a second button among the plurality of second buttons, wherein the hardware processor performs display control such that the first button highlighted by the first focus highlight is displayed in a display mode different from a display mode of other first buttons which are not highlighted from among the plurality of first buttons, and such that the second button highlighted by the second focus highlight is displayed in a display mode different from a display mode of other second buttons which are not highlighted from among the plurality of second buttons, control display so that the first focus highlight highlights a first button among the plurality of first buttons on which a first imaging condition for a first imaging session from among the plurality of imaging conditions is displayed, after completion of the first imaging session in the first imaging condition, display an image taken in the first imaging condition on the associated second button, controls display of the second focus highlight to highlight the second button on which the image taken in the first imaging condition is displayed, and transition the first focus highlight to highlight another first button among the plurality of first buttons on which a second imaging condition for a next imaging session is displayed, such that after completion of the first imaging session and before completion of the next imaging session, the first focus highlight highlights said another first button on which the second imaging condition is displayed and the second focus highlight concurrently highlights the second button on which the image taken in the first imaging condition of the completed first imaging session is displayed; and control a transition destination of at least one of the first focus highlight and the second focus highlight according to a type of the next imaging session performed after the first imaging session in the first imaging condition.

* * * * *